(12) United States Patent
Monty

(10) Patent No.: US 12,097,081 B2
(45) Date of Patent: *Sep. 24, 2024

(54) LASER BASED COMPUTER CONTROLLED DENTAL PREPARATION SYSTEM

(71) Applicant: Convergent Dental, Inc., Needham, MA (US)

(72) Inventor: Nathan P. Monty, Shrewsbury, MA (US)

(73) Assignee: Convergent Dental, Inc., Waltham, MA (US)

( * ) Notice: Subject to any disclaimer, the term of this patent is extended or adjusted under 35 U.S.C. 154(b) by 520 days.

This patent is subject to a terminal disclaimer.

(21) Appl. No.: 16/774,215

(22) Filed: Jan. 28, 2020

(65) Prior Publication Data

US 2020/0188059 A1 Jun. 18, 2020

Related U.S. Application Data

(60) Continuation of application No. 15/488,017, filed on Apr. 14, 2017, now Pat. No. 10,631,951, which is a (Continued)

(51) Int. Cl.
*A61C 1/00* (2006.01)
*A61B 1/06* (2006.01)
(Continued)

(52) U.S. Cl.
CPC .............. *A61C 1/0046* (2013.01); *A61B 1/06* (2013.01); *A61B 1/24* (2013.01); *A61C 1/0015* (2013.01); *A61C 17/02* (2013.01); *A61C 9/0053* (2013.01)

(58) Field of Classification Search
CPC ............ A61B 18/20; A61B 2018/2035; A61B 2018/20351; A61B 2018/20355; A61B 2018/20359; A61B 2018/00571; A61B 2018/00577; A61B 2018/00636; A61B 2018/00642; A61B 2018/0066; A61N 5/06; A61N 5/0601; A61N 5/0603;
(Continued)

(56) References Cited

U.S. PATENT DOCUMENTS 4,711,630 A 12/1987 Durr et al.
4,826,431 A 5/1989 Fujimura et al.
(Continued)

FOREIGN PATENT DOCUMENTS

DE 19533350 A1 5/1996
DE 102008053964 A1 5/2010
(Continued)

OTHER PUBLICATIONS

Assa, Shlomo, et al. "Ablation of Dental Hard Tissues with a Microsecond Pulsed Carbon Dioxide Laser Operating at 9.3-(mu)m with an Integrated Scanner," Lasers in Dentistry XIV, Proc. of SPIE, vol. 6843, 2008, pp. 1-7.
(Continued)

*Primary Examiner* — Ahmed M Farah
(74) *Attorney, Agent, or Firm* — Goodwin Procter LLP

(57) ABSTRACT

A dental tissue treatment apparatus and associated methods includes a feedback-controlled beam guidance system for directing treatment to a defined area of dental tissue.

20 Claims, 5 Drawing Sheets

Related U.S. Application Data division of application No. 13/603,165, filed on Sep. 4, 2012, now Pat. No. 9,622,833.

(60) Provisional application No. 61/530,761, filed on Sep. 2, 2011.

(51) Int. Cl.
*A61B 1/24* (2006.01)
*A61C 17/02* (2006.01)
*A61C 9/00* (2006.01)

(58) Field of Classification Search
CPC .. A61N 5/0606; A61C 1/0046; A61C 1/0053; A61C 1/08; A61C 1/088; A61C 1/10; A61C 1/12
USPC .............. 606/4–6, 8–13, 16–19; 607/88–93; 433/29–31; 128/898
See application file for complete search history.

(56) References Cited

U.S. PATENT DOCUMENTS

| | | | |
|---|---|---|---|
| 4,874,315 | A | 10/1989 | Featherstone et al. |
| 5,051,823 | A | 9/1991 | Cooper et al. |
| 5,310,471 | A | 5/1994 | Markle et al. |
| 5,342,198 | A | 8/1994 | Vassiliadis et al. |
| 5,364,390 | A | 11/1994 | Taboada et al. |
| 5,388,987 | A | 2/1995 | Badoz et al. |
| 5,401,171 | A | 3/1995 | Paghdiwala |
| 5,456,603 | A | 10/1995 | Kowalyk et al. |
| 5,538,425 | A | 7/1996 | Reeves et al. |
| 5,622,501 | A | 4/1997 | Levy |
| 5,748,663 | A | 5/1998 | Chenausky |
| 5,833,456 | A | 11/1998 | Davis et al. |
| 5,846,080 | A | 12/1998 | Schneider |
| 5,897,314 | A | 4/1999 | Hack et al. |
| 6,083,218 | A | 7/2000 | Chou |
| 6,198,762 | B1 | 3/2001 | Krasnov |
| 6,270,342 | B1 | 8/2001 | Neuberger et al. |
| 6,339,913 | B1 | 1/2002 | Leon Fong et al. |
| 6,482,199 | B1 | 11/2002 | Neev |
| 6,558,372 | B1 | 5/2003 | Altshuler |
| 6,558,374 | B1 | 5/2003 | Brugger et al. |
| 6,610,053 | B1 | 8/2003 | Rizoiu et al. |
| 6,663,386 | B1 | 12/2003 | Moelsgaard |
| 6,679,837 | B2 | 1/2004 | Daikuzono |
| 6,709,269 | B1 | 3/2004 | Altshuler |
| 6,758,844 | B2 | 7/2004 | Neuberger |
| 7,163,400 | B2 | 1/2007 | Cozean et al. |
| 7,270,543 | B2 | 9/2007 | Stookey et al. |
| 7,632,264 | B2 | 12/2009 | Schafer |
| 7,748,979 | B2 | 7/2010 | Nahlieli |
| 7,813,790 | B2 | 10/2010 | de Josselin de Jong et al. |
| 8,029,501 | B2 | 10/2011 | Miller |
| 9,622,833 | B2 * | 4/2017 | Monty ................... A61C 17/02 |
| 10,631,951 | B2 * | 4/2020 | Monty ................... A61C 17/02 |
| 2003/0100824 | A1 | 5/2003 | Warren et al. |
| 2004/0024388 | A1 | 2/2004 | Altshuler |
| 2006/0189965 | A1 | 8/2006 | Litvak et al. |
| 2006/0195072 | A1 | 8/2006 | Miller |
| 2007/0121786 | A1 | 5/2007 | Okawa et al. |
| 2007/0189353 | A1 | 8/2007 | Monty |
| 2008/0160477 | A1 | 7/2008 | Stookey et al. |
| 2009/0061391 | A1 | 3/2009 | Lukac et al. |
| 2009/0322541 | A1 | 12/2009 | Jones et al. |
| 2010/0021867 | A1 | 1/2010 | Altshuler et al. |
| 2010/0106146 | A1 | 4/2010 | Boitor et al. |
| 2010/0185188 | A1 | 7/2010 | Boutoussov et al. |
| 2010/0190129 | A1 | 7/2010 | Paz |
| 2010/0227296 | A1 | 9/2010 | Mandelis et al. |

FOREIGN PATENT DOCUMENTS

| | | |
|---|---|---|
| DE | 102009005194 A1 | 7/2010 |
| EP | 0437955 A1 | 7/1991 |
| EP | 2281528 A1 | 2/2011 |
| JP | 10277057 | 10/1998 |
| JP | H10277057 | 10/1998 |
| JP | H10277057 A | 10/1998 |
| JP | 2001161713 A | 6/2001 |
| JP | 3638191 B2 | 4/2005 |
| JP | 05245165 B2 | 7/2013 |
| WO | WO-97/10768 A2 | 3/1997 |
| WO | WO-2004/006793 A1 | 1/2004 |
| WO | WO-2007038975 A1 | 4/2007 |
| WO | WO-2008072033 A1 | 6/2008 |
| WO | WO-2009/052866 A1 | 4/2009 |
| WO | WO-2010/083825 A1 | 7/2010 |
| WO | WO-2011014802 A2 | 2/2011 |

OTHER PUBLICATIONS

Fan, Kenneth, et al. "A High Repetition Rate TEA C02 Laser Operating at lambda=9.3-(mu)m for the Rapid and Conservative Ablation and Modification of Dental Hard Tissues," Lasers in Dentistry XII, Proc. of SPIE, vol. 6137, 2006, pp. 1-9.

International Search Report and Written Opinion for International Patent Application No. PCT/US2010/043968 dated Apr. 20, 2011 (8 pages).

International Search Report and Written Opinion for International Patent Application No. PCT/US2011/023483 dated Jan. 25, 2012 (15 pages).

International Search Report and Written Opinion for International Patent Application No. PCT/US2012/053684 dated Mar. 4, 2013 (14 pages).

International Search Report and Written Opinion for International Patent Application No. PCT/US2011/023483 dated Jan. 25, 2012 (16 pages).

International Search Report for International Patent Application No. PCT/US2010/043968 dated Apr. 20, 2011 (14 pages).

Fan, Kenneth, et al. "A High Repetition Rate Tea C02 Laser Operating at lambda=9.3-(mu)m for the Rapid and Conservative Ablation and Modification of Dental Hard Tissues," Lasers in Dentistry XII, Proc. of SPIE, vol. 6137, 2006, pp. 1-10.

International Search Report and Written Opinion for International Patent Application No. PCT/US2012/053684 dated Feb. 22, 2013 (14 pages).

Ertl, et al., "Hard Tissue Ablation With Pulsed CO2 Lasers", SPIE vol. 1800 pp. 176-181.

Gerold K.H. Eyrich, "Laser-osteotomy induced changes in bone", Medical Laser Application 20 (2005) 25-36.

M. Frentzen, et al., "Osteotomy with 80µs CO2 laser pulses—histological results", Lasers Med Sci (2003) 18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016.1199743 (published online Jun. 27, 2016).

Ivanenko, et al., "Hard tissue ablation with sub-µs CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsurgical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

(56) References Cited

OTHER PUBLICATIONS

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

\* cited by examiner

| Feature | Min Val. | Nominal Val. | Max Val. | Unit |
|---|---|---|---|---|
| Wavelength | 9 | 9.25 - 9.4 | 10 | µm |
| Pulse energy | 0.1 | 11 | 30 | mJ |
| Pulse length | 0.1 | 20 | 30 | µsec |
| Pulse repetition rate | 0.1 | 0.5 to 2 | 4 | kHz |
| Fluence at focus | 0.14 | 7.94 | 50 | J/cm2 |
| Energy profile | Top Hat, Gaussian, Donut, Random | | | |
| Condition of tooth | Wet, Dry, Clean Cut, Sterilized, Fractured | | | |
| Rate at which galvos can adjust mirrors | 10 | 2500 | 100,000 | steps per second |
| Number of mirrors | 1 | 2 | 3 | # |
| Displacement of the laser at focus due to an adjustment of a mirror | 12.5 | 250 | 2000 | um |
| Shape of treatment area | Triangle, Square, Rectangle, Hexagon, Other polygons, Circle, Oval | | | |
| Size of treatment area | 4 | 15000 | $2.25 \times 10^8$ | um2 |
| Depth of treatment area | 12.5 | 50 | 50000 | um |
| Size of the spot of the CO2 laser | 0.03 | 0.042 | 0.2 | cm |
| Length of a segment of a perimeter that can be programmed as the treatment area | 2 | 50 | 150000 | um |
| Treatment time | 5 | 0.1 x 10^6 | 120 x 10^6 | usecs |
| Pattern of scanning | Random, Raster, Circular, Any Pattern | | | |
| Dimensions of the tapering portion of the hand piece (from galvos to 90 deg. turning optic) | 5 | 20 | 45 | Degrees |
| Dimensions of the portion of the hand piece that can be inserted into the patient's mouth (from turning optic to tip) | 6.25 | 12.5 | 25 | mm |
| Focal length of the first lens (upstream of galvos) | 2 | 7.5 | 180 | inches |
| Angles at which the turning optic can change the angle of the incident laser beam | 22.5 | 45 | 67.5 | degrees |

FIG. 7

LASER BASED COMPUTER CONTROLLED DENTAL PREPARATION SYSTEM

RELATED APPLICATIONS

This application is a continuation of and claims priority to and the benefit of U.S. patent application Ser. No. 15/488,017, filed on Apr. 14, 2017, which is a divisional of and claims priority to and the benefit of U.S. patent application Ser. No. 13/603,165, filed on Sep. 4, 2012, which claims priority to and the benefit of U.S. Provisional Patent Application Ser. No. 61/530,761, filed on Sep. 2, 2011, the entire contents of each of which are hereby incorporated by reference in their entireties.

FIELD OF THE INVENTION

This invention relates generally to the viewing, fluorescing, and scanning of electromagnetic radiation for the prevention and treatment of dental hard and soft tissue with a pulsed laser dental treatment device.

BACKGROUND

Dental caries (commonly known as "cavities") is a chronic infectious disease that is extremely difficult to completely eradicate. Tooth decay is caused by the demineralization of the tooth structure primarily originating in the enamel (hard tissue). Dental enamel is a thin layer, typically 1 to 2 mm thick, composed of a crystal-like structure of carbonated hydroxyapatite comprising 96% of enamel by weight and approximately 85% by volume. The balance of enamel, 15% by volume, is made up of water, protein, and lipid. Tooth decay is the result of dental acids, created by bacteria metabolizing sugars, which in turn de-mineralize the hydroxyapatite. The bacteria create a biofilm after 24 hours, referred to as plaque, which is soft and pliable, but after about 10 days the plaque hardens significantly to form dental calculus or tartar.

The majority of tooth decay occurs in the occlusal surface (top surface) and in unexposed areas between teeth. The lingual (back surface) and buccal (front surface) are relatively smooth compared to the occlusal surface, and therefore, trap less sugars to be metabolized resulting in relatively less dental acid and less decay than that in the occclusal surface and the unexposed areas between teeth. Decay is most likely in areas that cannot be brushed and cleaned easily such as pits and fissures on the occlusal surface, areas under the gums, and contact surfaces between the teeth.

Nevertheless, there has been a remarkable decline in dental caries over the last 60 years due to various new detection techniques such as digital x-rays, 3-D x-rays and fluorescence, prevention techniques including fluoride treatments and sealants, and new or improved treatment techniques including higher speed dental drills, smaller stronger burs, various wavelength laser technology, and ultrasonic cleaning equipment.

Detection: Analog x-rays have progressed to digital x-rays, and to cone beam 3-D x-rays, which have a higher resolution than the analog x-rays and are stored digitally while progressively using less and less radiation. Recently optical fluorescence has also been used to identify the bacterium that leads to tooth decay. Removing the fluorescing bacteria removes the carious tissue.

Prevention: Various fluoride treatments, new toothpastes, and mouthwashes have been introduced that re-mineralize the enamel, specifically with fluorapatite which has a higher resistance to dental acids than hydroxyapatite. Additionally flowable composites (commonly called epoxies) are referred to as "sealants," and are added to the occlusal surface to prevent bacteria from getting down into pits and fissures.

Treatment: Dental drills have progressed from motor driven rope mechanisms to compressed air driven devices, and to electrical motor driven devices. The Food and Drug Administration (FDA) has approved five different laser types at seven different wavelengths for a variety of dental indications. There are single wavelength dental laser devices, multiple wavelength devices, and q-switched, continuous and pulsed laser products. There are various dental laser hand pieces and delivery mechanisms, but all of these laser products are manufactured to maximally or minimally couple into water. Peak water absorption is sought to cut enamel because, as previously stated, water is only a 4% or less constituent by weight, so peak water absorption is required to vaporize water thereby fracturing the enamel, albeit slowly. Minimal water absorption is sought to cut soft tissue, gums and cheeks, so that the blood is cauterized and bleeding is minimized.

Recently a new laser based dental treatment system was developed that employs a mid-infrared wavelength laser that couples primarily into hydroxyapatite and partially into water. The advantage of coupling into hydroxyapatite, which constitutes about 96% of hard tissue by weight, is faster cutting with greater resolution, while partially coupling into water allows for faster soft tissue cutting while cauterizing avoiding bleeding.

In parallel to the above-described dental technology advances, optical scanners, or spinning mirrors, have been used in material processing applications for more than three decades. The advantage of using scanning mirrors to reposition optical energy is that high accuracy positioning can be achieved while overcoming a minimal amount of inertia. Low inertia allows the positioning system to accelerate and decelerate rapidly while maintaining high positional accuracy. Over the last three decades, various spinning mirror geometries have evolved creating smaller, faster movements without compromising accuracy.

Despite these advances, laser-based dental treatment systems face several challenges. One of the most common problems relates to the shape of the area to be treated. A cavity in a tooth rarely has a regular shape such as a square, circle, or an oval. In order to fully treat the affected area using previously known methods, the operator typically treats a regular-shaped area that encompasses the affected area. This, however, can cause damage to tissue that is within the encompassing area but that is not affected.

There is yet another problem in treating even a regular-shaped area. The operator must be able to hold the hand piece used to direct a laser beam to the treatment area extremely steady and then be able to move it carefully within a selected area. Laser beams used for treatment are generally very powerful, and slight movement of the operator's hand or by the patient can cause the laser beam to be directed to tissue that does not require any treatment and can cause damage thereto. Furthermore, within the selected area, the laser energy must be applied uniformly, i.e., the operator must direct substantially the same amount of energy to each point within the selected treatment area. As the overall treatment area is typically on the order of a few square centimeters or even smaller, manually directing a laser beam to the desired treatment area is difficult and error prone.

Therefore, there is a need for improved systems and methods of laser based dental treatment.

SUMMARY

Various embodiments of the present invention facilitate treatment of various dental infections with high accuracy, causing significantly less pain by mitigating or avoiding unnecessary treatment of unaffected areas. This is achieved, in part, by employing a computer-controlled optical system to direct a laser beam to a selected treatment area. The treatment area can be selected as a regular shape and also as a polygon that approximates the area that is actually affected. Computerized control of the optical system allows the laser beam to stay within the selected treatment area while simultaneously ensuring that the selected area is covered, i.e., the laser energy is directed in a substantially uniform manner within the selected treatment area. The energy profile of the laser beam at or near the treatment surface can also be controlled, in part, by adjusting the focal point of the laser beam. Selecting a suitable energy profile can further aid in uniformly treating the affected area.

Accordingly, in one aspect, embodiments of the present invention feature an apparatus for dental tissue treatment, that includes an optical system for directing a laser beam to dental tissue being treated. The optical system adjusts an energy profile of the laser beam at a location in proximity to the dental tissue. The apparatus also includes a feedback-controlled beam guidance system for targeting the laser beam within a specified area of a surface of the dental tissue.

In some embodiments, the optical system includes a lens. A focal length of the lens can be in a range from about 2 inches to about 15 feet. The energy profile may be selectable, e.g., by adjusting the optical system so as to adjust the focal length. The energy profile may be selected from a top-hat profile, a Gaussian profile, and a doughnut-shaped profile.

In some embodiments, the feedback-controlled beam guidance system includes a mirror, a galvanometer that includes (i) an actuator for adjusting a position of the mirror, and (ii) a sensor for determining the position of the mirror. The beam guidance system also includes a controller for controlling the actuator in a step, in response to the determined position of the mirror relative to a desired position of the mirror. The feedback-controlled beam guidance system may include two mirrors having axes of rotation disposed at about 90 degrees with respect to each other. A rate at which the controller moves the actuator may be in a range of about 10 steps per second to about 100,000 steps per second. Moving the actuator in one step may cause the laser beam at the surface of the dental tissue to be displaced in a range of about 2 micrometers up to about 15 millimeters.

In some embodiments, the desired position of the mirror is determined according to the specified area of the surface of the dental tissue. The desired position of the mirror may be determined according to a tracing pattern of the laser beam on the surface of the dental tissue. The tracing pattern can be a spiral trace, raster trace, and random trace. The specified area of the surface of the dental tissue is one of a triangle, a square, a rectangle, an oval, a circle, and a polygon. In some embodiments, the specified area of the surface of the dental tissue is a closed area of a user-defined shape having a perimeter that has several segments. The length of one segment can be in a range from about 2 µm up to about 15 mm. The specified area of the surface of the dental tissue may in a range of about 4 $\mu m^2$ up to about 2.25 $cm^2$. As such, the specified area may approximate the affected area.

In some embodiments, the apparatus also includes a hand-held unit having a tip that can be disposed adjacent to the dental tissue being treated. In addition, the apparatus includes a housing containing the optical system and the beam guidance system. The hand-held unit can be attached to the housing, whereby the laser beam is activated only if the hand-held unit is attached to the housing. The apparatus may also include a turning optic disposed within the hand-held unit.

In some embodiments, the apparatus includes an illumination system for illuminating at least a portion of the specified area of the surface of the dental tissue. The illumination system includes a light source and an optical system for directing and optionally collimating the illuminating light. The optical system may be adapted for focusing the light, in addition to directing and optionally collimating the light. In some embodiments, the illumination system includes a light source and a collector for reflecting light emitted by the light source, and an optical system for directing and optionally collimating the illumination light.

In some embodiments, the apparatus includes a cleansing system contained in the hand-held unit. The cleansing system may include water and/or air supply. The laser beam used for treatment may be a $CO_2$ laser beam. The $CO_2$ laser beam may have a spot size in range from about 0.03 µm up to about 0.2 cm. The apparatus may also include a marking laser beam, and the marking laser beam can be obtained from a gas or a laser diode in the range of about 500 nm up to about 700 nm, such as a red or green He—Ne laser beam.

In some embodiments, the apparatus includes vision system. The vision system includes an imaging system and a transfer lens. The imaging system may also include an optical filter and/or a variable focusing lens system. The apparatus may also include a shroud configured to be positioned inside a person's mouth. In some embodiments, the apparatus includes an air path for forming an air curtain to effectively stop any foreign substance from entering the apparatus.

In another aspect, embodiments of the present invention feature a method for dental tissue treatment. The method includes directing a laser beam toward dental tissue being treated, such that the laser beam has a certain energy profile at a location in proximity to the dental tissue. The method also includes targeting the laser beam within a specified area of a surface of the dental tissue via a feedback-controlled beam guidance system. The directing step may be performed using a lens having a focal length in a range from about 2 inches to about 15 feet. The energy profile may be selectable and can be one of a top-hat profile, a Gaussian profile, and a doughnut-shaped profile.

In some embodiments, the targeting step includes reflecting the laser beam using a mirror and determining a position of the mirror. The method also includes comparing the determined position of the mirror with a desired position of the mirror, and controlling the position of the mirror according to the comparison of the determined and desired positions of the mirror. Each of the reflecting, determining, comparing, and adjusting steps may be repeated at a rate in the range of about 10 steps per second to about 100,000 steps per second. The reflecting step may include reflecting the laser beam using two mirrors having axes of rotation disposed at about 90 degrees with respect to each other.

In some embodiments, the method also includes determining the desired position of the mirror according to the specified area of the surface of the dental tissue. The desired position of the mirror may be determined according to a tracing pattern of the laser beam on the surface of the dental tissue. The tracing pattern can be one of a spiral trace, raster trace, and random trace. The treatment method may also include specifying a shape, size, or both of the specified area of the surface of the dental tissue. The area of the surface of the dental tissue may be identified by specifying a closed area of a user-defined shape having a perimeter having several segments. A direction of the laser may be modified beam using a turning optic.

In some embodiments, the treatment method includes illuminating at least a portion of the specified area of the surface of the dental tissue. The laser beam can be a $CO_2$ laser beam, and the treatment method may include ablating the dental tissue. The ablated tissue can be soft tissue, hard tissue, or both. In some embodiments, prior to the ablating step, the specified area of a surface of the dental tissue is marked using a gas or laser diode in the range of about 500 nm up to about 700 nm, such as a red or green He—Ne laser beam.

In some embodiments, the directing step includes focusing the laser beam such that a focal point of the focused laser beam is located substantially at a surface of the dental tissue. The focal point of the focused laser beam may also be in proximity of a surface of the dental tissue. For example, the focal point can be above the surface of the dental tissue, or below the surface of the dental tissue.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means±10% and, in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 7 shows various parameters of the laser system and the ranges of the parameters.

DESCRIPTION

An electromagnetic energy output device is disclosed for implementing procedures on hard tissue, soft tissue and osseous bone. The electro-magnetic energy level and rate output from the device can be tailored to the different dental procedures of cutting or ablating soft, hard or osseous tissue, and also for decontamination, cleaning periodontal pockets, pain reduction, and bio stimulation procedures. See PCT/US2010/043968 and PCT/US2011/023483 for high power treatment lasers suitable for use herewith, the disclosures of which are incorporated by reference herein in their entirety.

Figure 1:
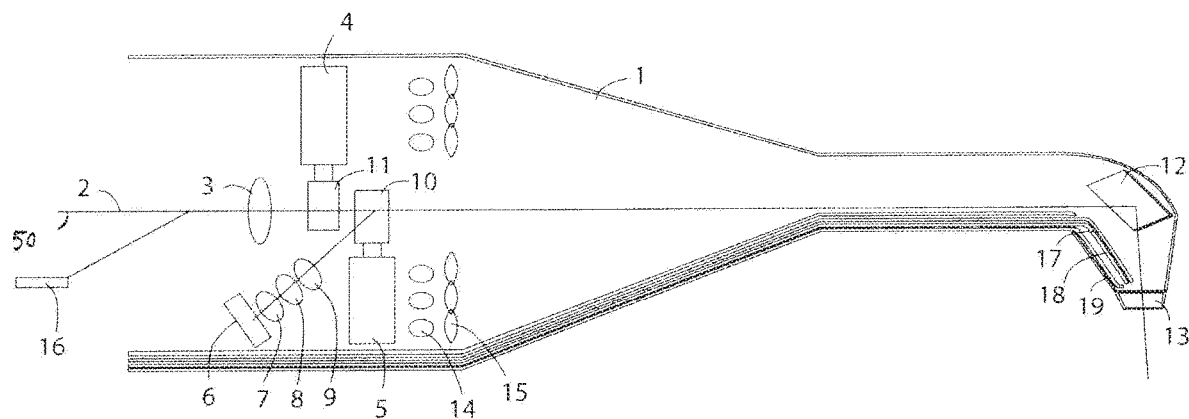
FIG. 1 shows a cross-section of a typical dental hand-piece according to one embodiment of the invention for dental viewing, diagnosis, and treatment by means of a laser.

As depicted in FIG. 1, a high power treatment laser beam, such as a $CO_2$ laser beam, enters a dental hand-piece 1 on optical axis 2. The laser beam is directed through a focusing lens 3 and two computer controlled moving optical elements 4, 5. The focusing lens 3 may be located ahead of or behind the optical elements 4, 5. An image system may be integrated into the dental hand-piece 1, and the image system may include an imaging device 6 such as a CMOS or CCD camera chip, a lens system 7, a filter 8 and/or a focusing element such as an electro-static lens 9. The lens system 7 can include a transfer lens and/or a variable focus lens. The variable focus lens can be used to select a suitable energy profile of the laser beam, as described below. The imaging system may be located co-linearly with the optical axis 2 of the high power treatment laser beam by reflecting light rays received from the treatment area and traveling generally along the optical axis 2 off a mirror 10 or a mirror 11 coupled to the moving optical elements 4 or 5, respectively.

Regardless the location of the imaging system, the components thereof are configured such that light corresponding to the images of the area of the dental tissue being treated propagates substantially along the optical axis 2. As a result, an operator of the laser beam can view the received images during treatment, without having to replace the treatment device with a separate imaging device or without having to position simultaneously two devices in the patients mouth—one for treatment and the other for imaging. Moreover, the operator has substantially the same perspective as that of the treatment laser beam. This allows the operator to accurately monitor the effect of the laser beam precisely on the area of the dental tissue being treated during such treatment. This arrangement can also provide comfort to the patient, because the patient need not open his or her jaw so wide as to allow one access path for the treatment laser beam to the dental tissue and another viewing path, at a different angle, to the operator.

In some embodiments, an optical fluorescence system is integrated into the dental hand-piece 1. The fluorescence system generally includes an fluorescing light source (e.g., source of ultra-violet (UV) light) that is located similarly as the imaging device 6. The fluorescence system may use one or more of a lens system, filter, and a focusing element such that rays of substantially monochromatic light from the fluorescing source travel along the optical axis 2 to the dental region to be examined. If a certain area within that dental region is affected, e.g., due the presence of bacteria, the light reflected from that area typically has a peak wavelength different than that of the substantially monochromatic light. Those reflected light rays travel back along the optical axis 2 and may be viewed using the imaging system. The operator can analyze the received images to detect any affected areas requiring treatment.

FIG. 1 also depicts an optical element 12 that turns or reorients the optical axis 2 so as to increase the ergonometric design of the hand-piece 1. The optical element 12 is optional, however, and embodiments in which the optical axis 2 is not turned at about 90 degrees, as shown in FIG. 1, are within the scope of the invention. A shroud or cover 13 may be added to the hand-piece 1 to position the hand-piece, block the illuminating light (described below), and/or to prevent the treatment laser beam from reaching the dental tissue substantially outside the area to be treated. The shroud 13 may also support the dental hand-piece 1 when it is positioned in a patient's mouth.

In some embodiments, illumination diodes or diode lasers 14 are added to the hand-piece 1 to aid the imaging system, for example, by shining light in the viewing the area of the dental tissue being treated. Various light collection and focusing elements 15 (e.g., Fresnel lenses) may be used for collecting and guiding the light through the end opening of the hand-piece shroud 13 onto the dental tissue. In some embodiments, a marking laser 16 (described below in detail) is provided to provide visible light where the invisible treatment laser beam will be directed. The marking laser beam also travels along the high power treatment laser axis 2.

In some embodiments, the imaging system, the illumination system, the computer controlled optical elements 4, 5, and the focusing lens 3 are located in a housing, and the hand-piece 1 can be attached to the housing. If the hand-piece 1 is detached from the housing, the laser beam 50 turns off, thereby preventing accidental exposure to the laser beam.

Figure 2:
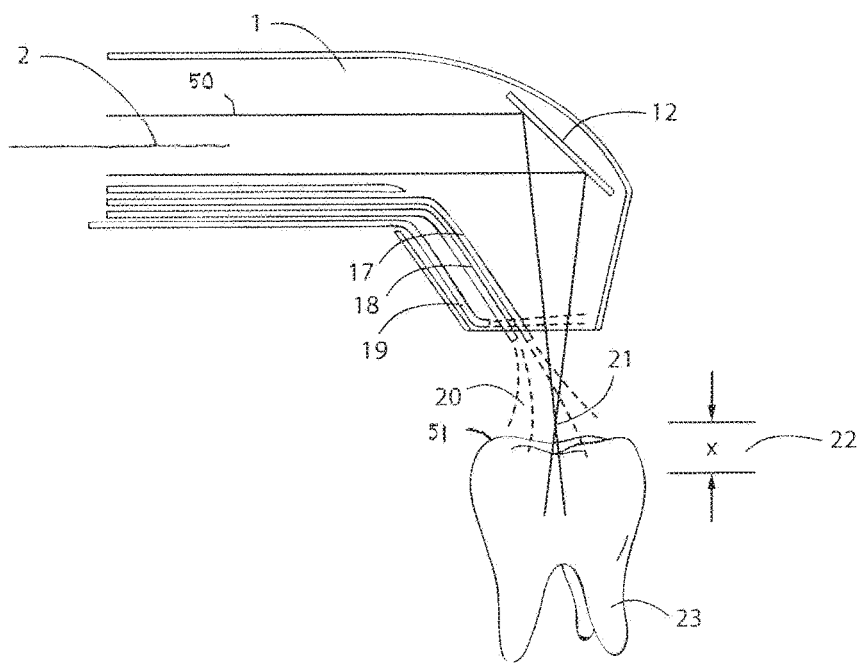
FIG. 2 shows the tip of the hand-piece depicted in FIG. 1 and focusing of the laser beam according to one embodiment of the invention.

With reference to FIG. 2, air and water paths 17, 18 are included in the hand-piece 1. The air and water paths 17, 18 are both optional. Using these paths, air, water, or a mixture thereof can be used to spray, clean, or dry the tooth before, during, and/or after treatment. The air and water mixture can create a water mist that generally aids in cutting of hard dental tissue by providing cooling. Air alone may be used to cut soft dental tissue or to dry or blow off dental tissue. An additional air path 19 is optionally added to provide an air flow near the opening of the hand-piece tip/shroud 13. The air path 19 creates a curtain of pressurized air across the opening in tip/shroud 13, blocking any water used in treatment and/or debris resulting from cutting from entering into the hand-piece and attaching to the mirror 12.

In the end portion of dental laser hand-piece 1, the high power treatment laser beam 50 reflects off the mirror 12 and focuses at a point of focus 21. Using a converging laser beam 50, a substantially flat mirror 12 can be used to focus the laser beam at or near the point 21. Alternatively or in addition, a multi-segment mirror or a concave mirror can be used to focus parallel or converging laser beams at the point of focus 21.

The location 21 at which the laser beam focuses, i.e., the laser beam's cutting depth with respect to the dental tissue 51, can be adjusted over a range "X" 22. Though FIG. 2 shows the point of focus 21 of the laser beam slightly above the surface 51 of the dental tissue, the point of focus 21 can be located at or below the surface 51. Adjusting the point of focus 21 of the laser beam at a distance from the surface 51 (i.e., above or below the surface 51) facilitates varying the energy density profile of the laser beam at the treatment surface 51. Thus, by adjusting the location of the point of focus 21, a laser of a suitable energy profile can be directed to the treatment area on the dental tissue surface 51.

Figure 3:
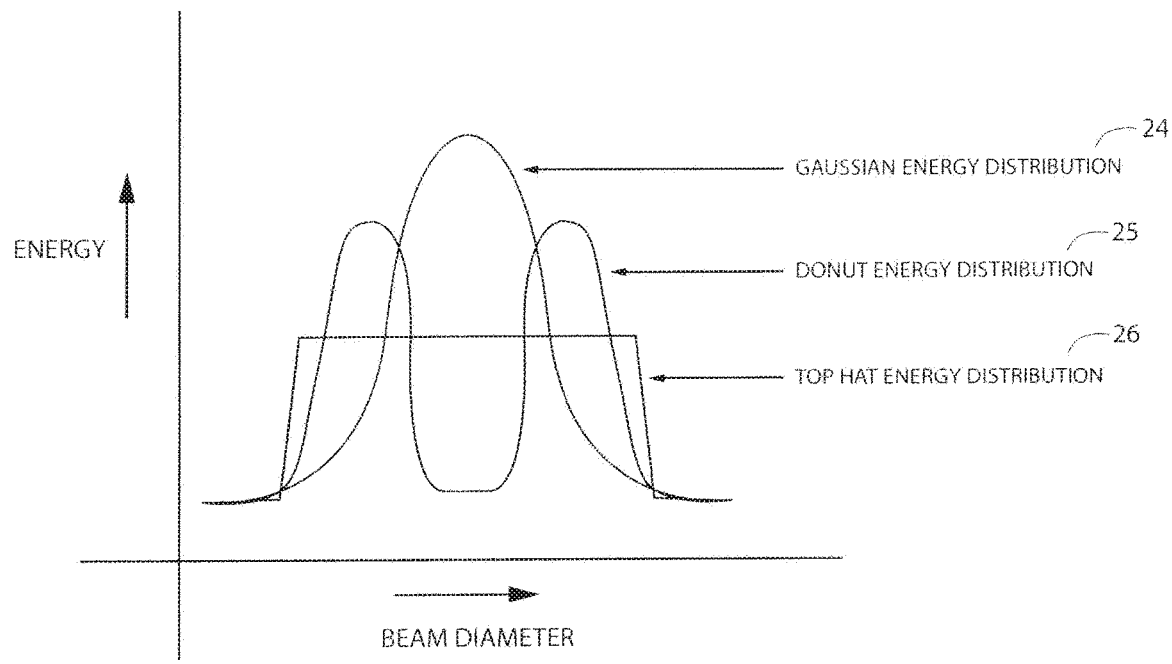
FIG. 3 shows some exemplary beam diameters versus energy distribution profiles across the focused beam diameters.

As depicted in FIG. 3, various energy distribution profiles can be generated at the treatment surface 51. In some embodiments, using a spherical optic a Gaussian energy distribution 24 is achieved and using non-spherical optics various other energy distributions such as a donut-shaped 25 distribution or a Top Hat 26 distribution can be achieved. Using different energy distribution profiles, accuracy of treatment can be improved. For example, the Gaussian profile 24 can be used to treat a relatively small affected area, while the Top Hat profile 26 can be used to treat a relatively large affected area. Moreover, using the Top Hat profile 26, laser energy can be directed more uniformly across a relatively large area, as opposed to applying significant amount of energy only to the center of the treatment area if an energy profile having a peak (such as the Gaussian profile 24) were used.

Figure 4:
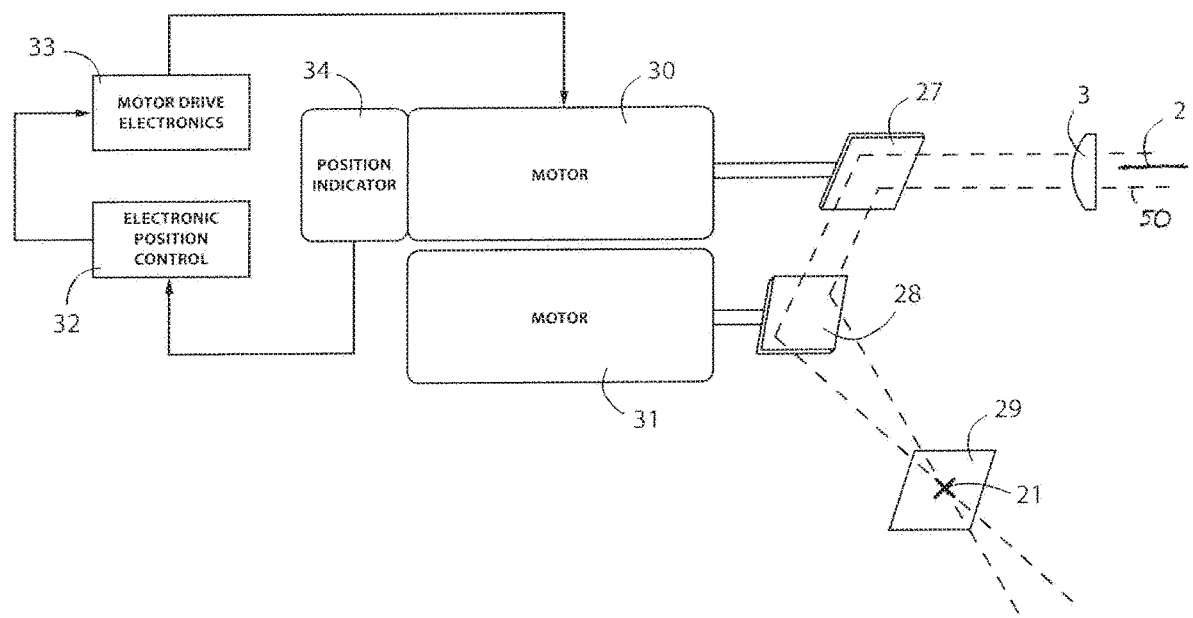
FIG. 4 shows a closed loop position control system including galvanometers and mirrors according to one embodiment of the invention.

With reference to FIG. 4, the high power treatment laser beam 50 passes through the focusing lens 3 and the focused beam is directed by spinning mirrors 27, 28. The spinning mirrors 27, 28 are computer controlled moving optical elements 4, 5 shown in FIG. 1 The spinning mirrors 27, 28 can be moved in steps such that the point of focus 21 of the treatment laser beam 50 can be moved along X and/or Y directions so as to cover substantially entirely a treatment area 29. The spinning mirrors 27, 28 can be controlled by a positional closed loop feedback system that includes motors 30, 31. The motors 30, 31 typically include a galvanometer including an actuator for adjusting positions of the spinning mirrors 27, 28. The positional loop associated with the motor 30 includes a sensor or position indicator 34, an electronic position control device 32, and the motor drive electronics 33. A second positional control loop (not shown), which may utilize one or more of the components 32-34, is associated with the motor 31.

Though FIG. 4 shows the dental tissue treatment area 29 as having a square shape, this is for illustrative purposes only. It should be understood that other shapes such as a triangle, polygon, circle, oval, etc., are within the scope of the invention. As explained in detail with reference to FIG. 6 below, in some embodiments, the treatment area 29 can be defined by the operator. The position control device 32 is provided with information about the treatment area 29. Such information may include the size and shape of the treatment area 29. The position indicator 34 determines the relative position of the point of focus 21 of the laser beam 50 within the treatment area 29 at a particular instance. Based on the relative position obtained from the position indicator 34, the position control device 32 can determine the movement of the motor 30 during the next step of operation. These steps are determined for each of the motors 30, 31 such that the laser beam 50 is substantially confined to the treatment area 29, and covers, i.e., treats the area 29 in a substantially uniform manner. Thus, the positional closed-loop feedback system enables an operator to select and/or define a treatment area that approximates only the affected area of an irregular shape, and to automatically treat the entire selected and/or defined area, without substantially affecting the other portions of the unaffected dental tissue adjacent to the treatment area.

Figure 5:
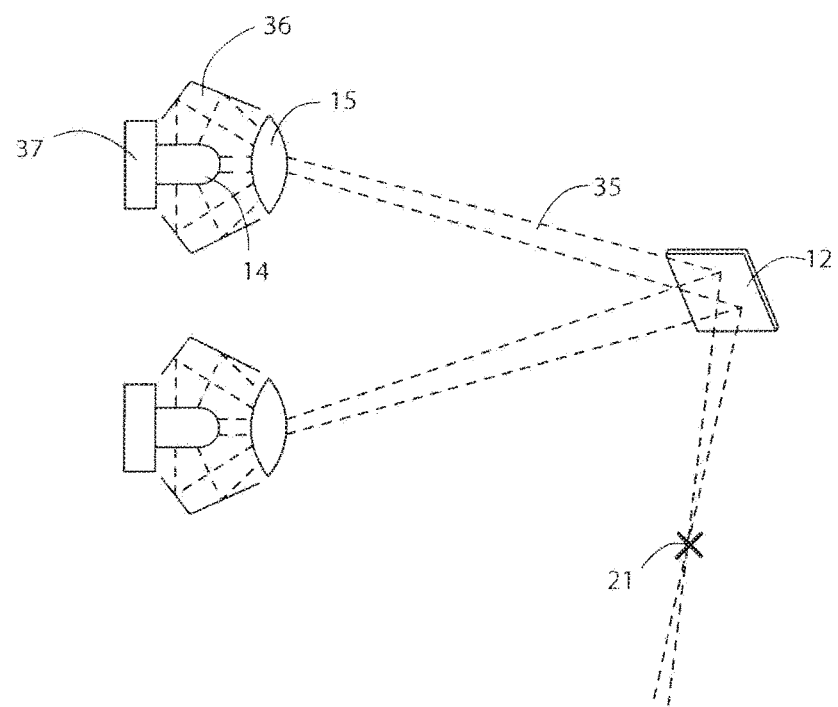
FIG. 5 shows a remote illumination system according to one embodiment of the invention.
Figure 5:
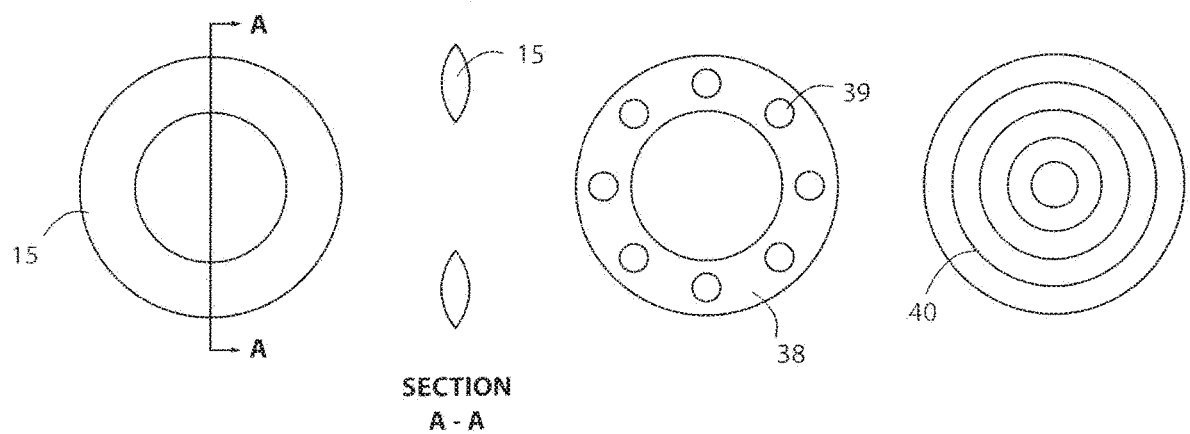

With reference to FIG. 5, light rays from the LED or laser diode light elements 14 are reflected by a collector 36 and can be collimated or focused by an optical element 15. The collimated/focused light rays are reflected off the dental hand-piece turning mirror 12 to the focus position 21, i.e., the point of focus of the high power treatment laser beam 50, as described above with reference to FIGS. 2 and 4. The LED/laser diode elements 14 can be mounted in the hand-piece 1 on a printed circuit board 37, for example. The focusing elements 15 can be formed using, for example, an optic 38 having lenslets 39, or a Fresnel lens 40. Alternatively or in addition, the light from the elements 14 can reflect off a polished interior of the hand-piece 1, so as to be guided to the treatment area through the opening in the tip/shroud 13 of the hand-piece 1.

Figure 6:
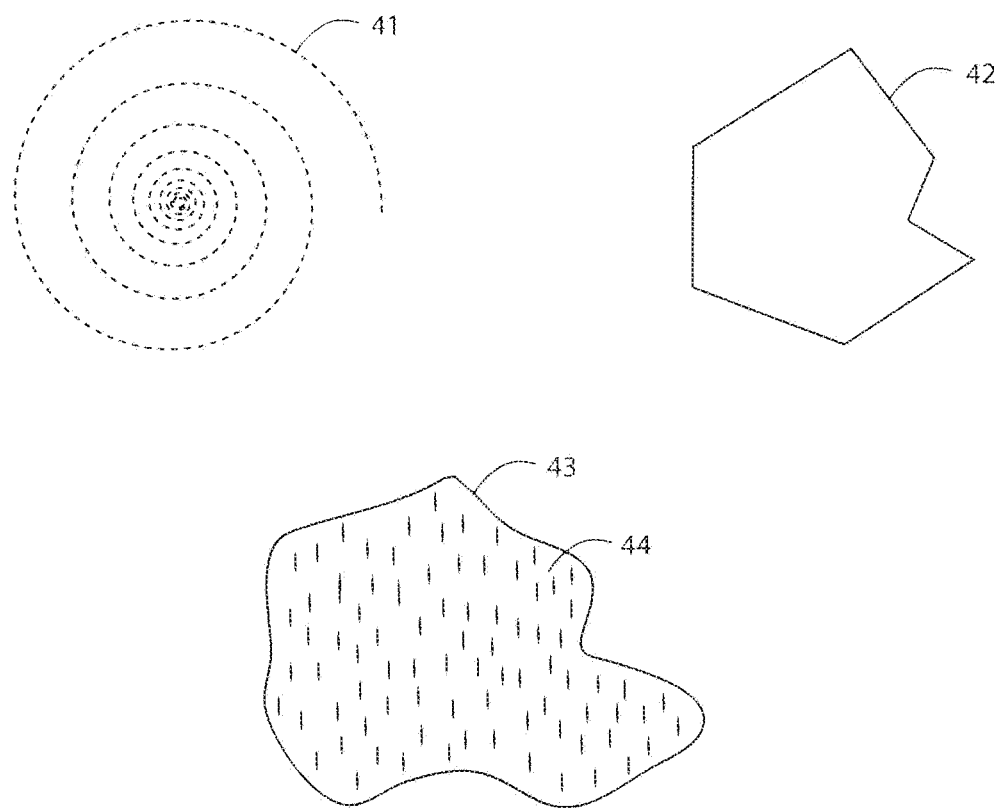
FIG. 6 shows some exemplary laser treatment areas and tracing patterns.

As depicted in FIG. 6, the treatment area 29 treated by the laser beam 50 that is moved using the two spinning mirrors 27, 28 as described above with reference to FIG. 4, can be a polygon 42 (i.e., a triangle, square, rectangle, hexagon, etc.), a circle or oval, or any operator defined shape 43. A user/operator may define the shape 43 as a closed area having a perimeter of short segments of length in the range about 12 μm to about 1.5 cm. In contrast to treating dental tissue areas of a fixed size and/or shape, such as a 4 mm×4 mm square, defining the shape 43 as a polygon of short segments enables the operator to precisely select virtually only the affected area of the dental tissue for treatment. As described above with reference to FIG. 4, substantially only the selected, i.e., affected, area can be treated by the laser beam, without unnecessarily exposing the adjacent unaffected tissue to the laser beam radiation.

During treatment, the mirrors 27, 28 and the associated positional control loops (shown in FIG. 4) are configured such that the laser pulses or a continuous power electromagnetic energy of the laser beam traces the entire treatment area 42 or 43 according to a pattern. As shown in FIG. 6, the tracing pattern can be a spiral pattern 41, a raster pattern, or a random pattern 44. When a laser beam impinges upon a spot in the treatment area 42 or 43, a plume of tissue material may be emitted. During the next step, moving the laser beam to a randomly selected location, as shown by the pattern 44, can avoid any interaction between the treatment laser beam and the plume, and, instead, the laser beam is directed to the tissue to be treated.

Prior to commencing treatment using the treatment laser beam as described above, it may be beneficial for an operator to ensure that the treatment laser beam would, in fact, impinge upon all of the treatment area in a uniform manner, and not impinge upon the tissue not to be treated. To this end, the marking laser 16 described above with reference to FIG. 1 can be used. The marking laser 16, e.g., a He—Ne laser, traces the treatment area 42 or 43 substantially similarly as the treatment laser beam would, because both laser beams are focused along the axis 2, and both laser beams are directed using the system schematically shown in FIG. 4. The marking laser 16, however, lacks power to ablate or adversely affect dental tissue in the area 42 or 43, and, hence, may not inadvertently damage the dental tissue within or adjacent to the treatment area 42 or 43.

Moreover, the marking laser 16 emits visible light, such as red light, so that the operator can see the tracing of the area 42 or 43 as the marking laser beam is moved, using the imaging system described above with reference to FIG. 1. Once the operator ensures that the marking laser 16 covers substantially the entire treatment area according to the selected tracing pattern (e.g., patterns 41, 44), and does not affect areas substantially outside the treatment area 42 or 43, the operator can activate the treatment laser beam, and treat the area, as described above. Using the marking laser 16 in combination with the computer-controlled feedback system to control the movement of laser beam, only the affected dental areas of virtually any size and shape can be treated effectively and easily, while mitigating or eliminating the risk of significant damage to the surrounding unaffected areas.

FIG. 7 shows a table identifying various system parameters such as energy densities, pulse width of the laser beam, length of a segment used to define a treatment area, etc. The ranges of the parameters, and their nominal values are also shown in the table.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. An apparatus for dental tissue treatment, the apparatus comprising:
   a laser source for generating a laser beam;
   an optical system for directing a laser beam to dental tissue being treated, whereby the laser beam has a selected energy profile at a location in proximity to the dental tissue; and
   a feedback-controlled beam guidance system adapted to:
      target the laser beam to impinge upon a first location within a specified area of a surface of the dental tissue; and
      displace the laser beam within the area in a step range of about 2 micrometers up to about 15 millimeters to a second location to avoid interaction between the displaced laser beam and a plume of tissue material emitted from the first location.

2. The apparatus of claim 1, wherein the optical system comprises a lens.

3. The apparatus of claim 2, wherein a focal length of the lens is in a range from about 2 inches to about 15 feet.

4. The apparatus of claim 1, wherein the energy profile is selectable and is selected from the group consisting of a top-hat profile, a Gaussian profile, and a doughnut-shaped profile.

5. The apparatus of claim 1, wherein the feedback-controlled beam guidance system comprises:
   a mirror;
   a galvanometer comprising (i) an actuator for adjusting a position of the mirror, and (ii) a sensor for determining the position of the mirror; and
   a controller for controlling the actuator in a step, in response to the determined position of the mirror relative to a desired position of the mirror.

6. The apparatus of claim 5, wherein the feedback-controlled beam guidance system comprises two mirrors having axes of rotation disposed at about 90 degrees with respect to each other.

7. The apparatus of claim 5, wherein a rate at which the controller moves the actuator is in a range of about 10 steps per second to about 100,000 steps per second.

8. The apparatus of claim 5, wherein moving the actuator in one step causes the laser beam at the surface of the dental tissue to be displaced in a range of about 2 micrometers up to about 15 millimeters.

9. The apparatus of claim 5, wherein the desired position of the mirror is determined according to the specified area of the surface of the dental tissue.

10. The apparatus of claim 9, wherein the desired position of the mirror is determined according to a tracing pattern of the laser beam on the surface of the dental tissue, the tracing pattern being selected from the group consisting of spiral trace, raster trace, and random trace.

11. The apparatus of claim 1, wherein the specified area of the surface of the dental tissue is one of a triangle, a square, a rectangle, an oval, a circle, and a polygon.

12. The apparatus of claim 1, wherein the specified area of the surface of the dental tissue is a closed area of a user-defined shape having a perimeter comprising a plurality of segments.

13. The apparatus of claim 12, wherein a length of one segment is in a range from about 2 μm up to about 15 mm.

14. The apparatus of claim 1, wherein the specified area of the surface of the dental tissue is in a range of about 4 $\mu m^2$ up to about 2.25 $cm^2$.

15. The apparatus of claim 1, further comprising:
   a hand-held unit having a tip disposable adjacent to the dental tissue being treated; and
   a housing containing the optical system and the beam guidance system, the hand-held unit being attachable to the housing, whereby the laser source is activated only if the hand-held unit is attached to the housing.

16. The apparatus of claim 15, further comprising a turning optic disposed within the hand-held unit.

17. The apparatus of claim 1, wherein the feedback-controlled beam guidance system is further adapted to, prior to targeting the laser beam to impinge upon a first location, deliver a marking laser to the area.

18. The apparatus of claim 17, wherein the feedback-controlled beam guidance system is adapted to displace the marking laser within the area according to a planned pattern of displacement of the laser beam.

19. The apparatus of claim 1, wherein the feedback-controlled beam guidance system is disposed between the laser source and the optical system.

20. A method for dental tissue treatment, comprising:
   directing a laser beam toward dental tissue being treated, whereby the laser beam has a selected energy profile at a location in proximity to the dental tissue; and
   targeting the laser beam to impinge upon a first location within a specified area of a surface of the dental tissue via a feedback-controlled beam guidance system; and
   displacing the laser beam within the area in a step range of about 2 micrometers up to about 15 millimeters to a second location to avoid interaction between the displaced laser beam and a plume of tissue emitted from the first location.

* * * * *